United States Patent [19]

Negersmith

[11] 4,009,999
[45] Mar. 1, 1977

[54] REAGENT SUPPLY CONTROL IN AUTOMATED FLUID ANALYSIS

[75] Inventor: Kent M. Negersmith, Carmel, N.Y.

[73] Assignee: Technicon Instruments Corporation, Tarrytown, N.Y.

[22] Filed: May 29, 1975

[21] Appl. No.: 582,059

[52] U.S. Cl. .............................. 23/230 R; 23/253 R
[51] Int. Cl.² .................. G01N 31/00; G01N 33/00
[58] Field of Search ......... 23/230 R, 230 B, 253 R, 23/259

[56] References Cited
UNITED STATES PATENTS

| | | | |
|---|---|---|---|
| 3,241,432 | 3/1966 | Skeggs et al. | 23/253 R X |
| 3,282,651 | 11/1966 | Ferrari et al. | 23/253 R |
| 3,525,591 | 8/1970 | Jungner et al. | 23/253 R |
| 3,572,994 | 3/1971 | Hochstrasser | 23/253 R X |
| 3,583,232 | 6/1971 | Isreeli et al. | 23/259 UX |
| 3,698,870 | 10/1972 | De Jong | 23/253 R |
| 3,764,268 | 10/1973 | Kosowsky et al. | 23/253 R |
| 3,781,120 | 12/1973 | Engelhardt | 356/244 |
| 3,912,456 | 10/1975 | Young | 23/253 R |

*Primary Examiner*—Joseph Scovronek
*Attorney, Agent, or Firm*—S. P. Tedesco; Stephen E. Rockwell

[57] ABSTRACT

Apparatus and method for analyzing successive liquid samples and conserving reagent. The method includes flowing a stream of discrete samples along a conduit from a source, which conduit includes a portion for reacting the successive samples with a reagent and a portion for analyzing the reaction product. It further includes introducing the reagent into the conduit upstream of the reaction portion to form a sample-reagent mixture, identifying the successive samples at the source, and responsive to such identification discontinuing the introduction of the reagent into the conduit and substituting therefore a pilot fluid displacing the mixture at the same flow rate along the reacting and analysis portions of the conduit.

6 Claims, 2 Drawing Figures

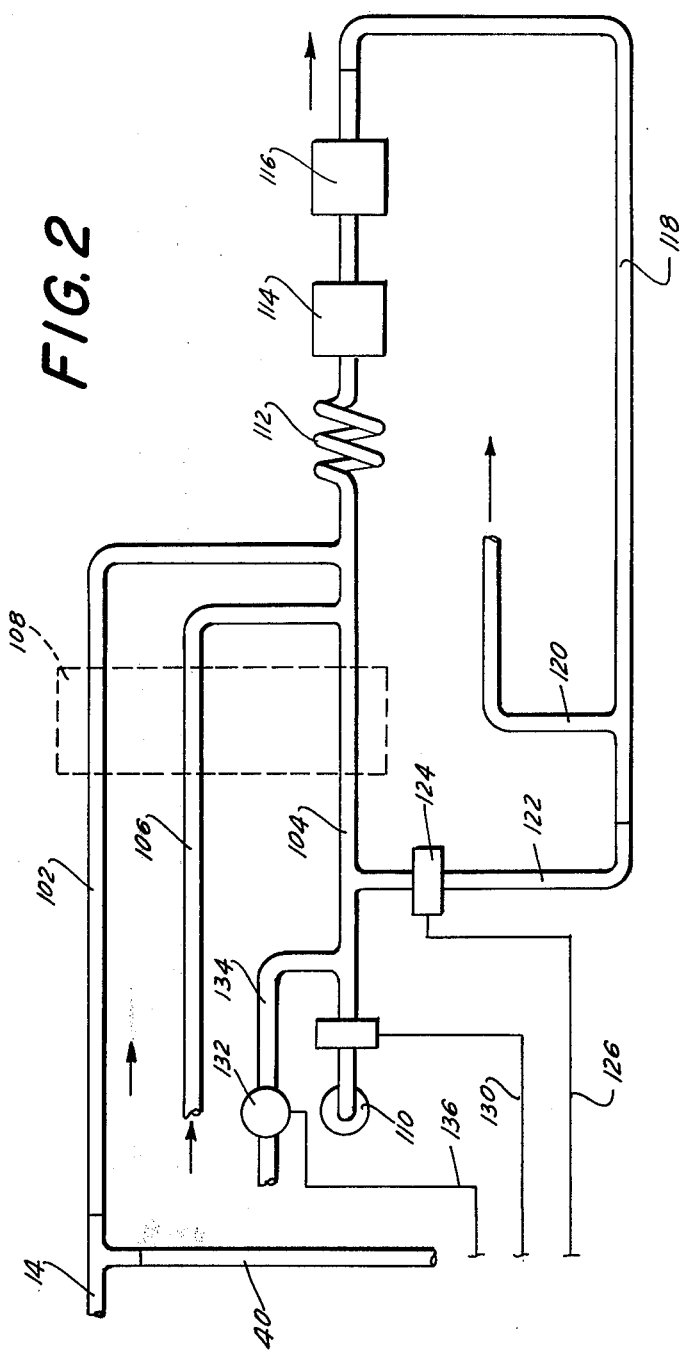

4,009,999

REAGENT SUPPLY CONTROL IN AUTOMATED FLUID ANALYSIS

BACKGROUND OF THE INVENTION

1. Field of the Invention

This invention relates to reagent conservation in continuous-flow quantitative sample analysis.

2. Prior Art

Known automated continuous-flow-type of quantitative sample analysis has many advantages over automated analysis of the batch type wherein aliquots of a liquid sample are dispensed into cuvettes each for analysis of a different constituent of the sample when mixed therein with a different reagent. The reaction product is analyzed in each cuvette. On the other hand, in such continuous-flow analysis of the multichannel type such as described, for example, in Skeggs et al U.S. Pat. No. 3,241,432 successive isolated samples flowing in a stream are split into aliquots flowing into respective ones of different manifolds in each of which the corresponding aliquot is joined and reacted with a continuously flowing stream of a different reagent for analysis of a reaction product in a flow-through cell for quantitation of a different constituent of the sample. The advantages of continuous-flow analysis include, among others, visual function monitoring by the operator of the system of computer monitoring for analysis verification, more simple construction with fewer moving parts giving rise to greater performance reliability, and versatility with reference to substitution or modification of one manifold from one sample constituent analysis to a different sample constituent analysis.

One drawback to such multichannel analyzers for multiple constituents of samples has been that sometimes not all of the analyses for which the equipment is set up have been required or ordered by physicians of particular blood samples, for example. So far as is known, such continuous-flow equipment has not been provided with a control device for identifying on each sample holder the particular analysis requirements of that sample to govern a responsive mechanism in the equipment which discontinues the reagent supply to one or more unneeded channels. Such termination of flow of unneeded reagents results in significant savings as the last-mentioned reagents may be numerous and/or costly.

The present invention contemplates overcoming such difficulties in continuous-flow analyzers in the prior art.

SUMMARY OF THE INVENTION

One object of the invention is to provide an improved continuous-flow analyzer having a control device for identifying with respect to each of successively flowed samples in a stream the reagent requirement of the sample, to govern a responsive mechanism in the equipment to meet the particular reagent requirement. Another object is to conserve reagent for an unneeded analysis of a constituent of a sample. Further objects will be apparent from the following detailed description of the presently preferred forms of the invention. Further, there is provided method and apparatus for analysis of successive liquid samples which includes flowing a stream of discrete samples along a conduit from a source, which conduit includes a portion for reacting the successive samples with a reagent and a portion for analyzing the reaction product, introducing the reagent into the conduit upstream of the reaction portion to form a sample-reagent mixture, identifying the successive samples at the source, and responsive to such identification discontinuing the introduction of the reagent into the conduit and substituting therefor a pilot fluid displacing the mixture of the same flow rate along the reacting and analysis portions of the conduit.

BRIEF DESCRIPTION OF THE DRAWINGS

In the drawings:

FIG. 2 is a fragmentary diagrammatic view illustrating an alternative form of manifold for use in the analyzer of FIG. 1.

DETAILED DESCRIPTION OF THE PREFERRED EMBODIMENTS

Figure 1:
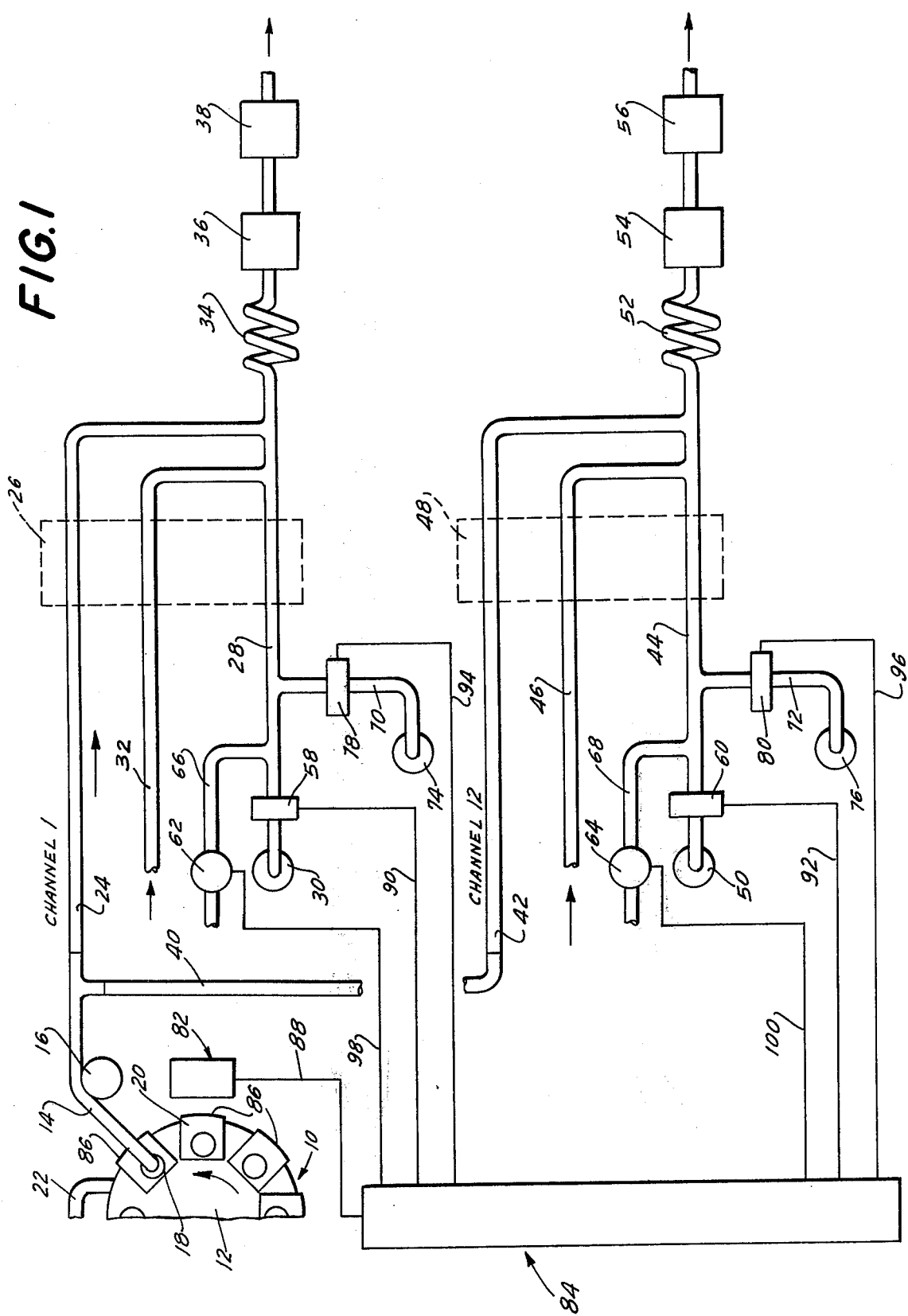
FIG. 1 is a broken, fragmentary diagrammatic view of a liquid sample analyzer embodying the invention.

In FIG. 1, there is indicated, generally at 10, a sample source. The source 10 may take the form of a sampler, such as illustrated in de Jong U.S. Pat. No. 3,134,263 and includes a turntable 12. The sampler includes an aspirating probe 14 for immersion in liquids of successive sample cups or holders in circular array on the turntable and containing a series of different samples which by way of illustration may be blood serum samples. Each sample holder of the series may be indexed on angular movement of the table 12 with respect to the probe 14. One such sampler holder is indicated at 18 and the next following holder 20. The sampler also includes a wash receptacle 22 containing a wash solution in which the probe 14 is immersed between successive samples. When the probe 14 leaves the sample liquid or the wash solution, air is aspirated into the probe and this air flow forms in a conventional way an immiscible fluid segment in the stream flowing in the probe 14 on reimmersion of the probe 14 into the other liquid, thus producing a segmented liquid stream, all liquid segments of which are bounded by a pair of such immiscible fluid segments. The probe 14 is provided with a movable support 16 which enables the probe to move between successive samples and to the wash solution between successive samples. The outlet end portion of the probe 14 is formed with a T connection, one outlet of which is coupled to the inlet end of a compressible pump tube 24 extending through a peristaltic pump 26 for flow therethrough of such a segmented stream.

A compressible pump tube 28 extends through the pump 26 and has an inlet end disposed in a liquid reagent source 30. Downstream from the pump 26, the outlet end of the tube 24 is coupled to the tube 28 intermediate the ends of the latter. A compressible pump tube 32, having an inlet end exposed to ambient air, extends through the pump and has an outlet end coupled to the tube 28 downstream of the pump and upstream of the coupling of the tube 24 to the tube 28. Progressively downstream of the last-mentioned coupling there are interposed in the tube 28 a mixing coil 34, a conventional heating bath 36 and a photometric flowcell 38.

When reagent is supplied to be combined with a sample, a stream of reagent from the source 30 flows in the tube 28 through the action of the continuously operated pump 26 and is segmented by gas supplied from the tube 32. The aforementioned segmented sample stream flowing in the tube 24 is added to the segmented reagent stream in the tube 28. Segments of sample are segmented by gas supplied in the last-mentioned reagent stream. Segments of sample and reagent are mixed in the coil 34 and the mixture, retaining the last-mentioned segmentation pattern, flows from the coil in the tube 28 to the heating bath 36 wherein the reagent reacts with the sample to produce a reaction product resulting in a change in the optical density. The reaction product of each successive reacted sample flows from the heating bath 36 through the tube 28 to the flowcell 38, which may take the form of the flowcell described in Bellinger et al U.S. Pat. No. 3,740,158, wherein the successive reaction products of the sample are photometrically analyzed for one constituent of interest in each sample prior to flowing to waste from the cell through the tube 28. The result of each analysis is conventionally displayed in a nonillustrated manner. The above-described manifold or channel for analysis of a constituent of such samples, say albumin for example is designated Channel 1, one of a plurality of channels for analysis of different constituents of such samples.

As shown in FIG. 1, the other outlet of the T connection of the probe 14 is coupled to the inlet end of a tube 40 in which a division of the segmented sample stream from the probe flows as will appear hereinafter. Any desired number of channels may branch off the tube 40. As herein illustrated, for the purpose of simplification of the drawings and description, only one further channel is shown, Channel 12. The last-mentioned channel has pump tubes 42, 44 and 46 extending through a continuously operated pump 48, similar to pump tubes 24, 28 and 32 and pump 26 described above. The inlet end of tube 42 is coupled to an outlet of the tube 40. The inlet end of tube 44 is disposed in a source 50 of a different liquid reagent. Tube 44 has interposed therein a coil 52, a heating bath 54 and a flowcell 56 which are similar to the above-described coil 34, heating bath 36 and a flowcell 38. Downstream of the cell 56 the tube 44 flows to waste. The constituent of such samples analyzed in Channel 12 may be glucose for example.

When in the analysis of any particular sample there is no requirement for analysis of albumin and/or glucose, such as the sample in the holder 18 of the sampler 10, the reagent supply to Channel 1 and/or Channel 12 is discontinued for that particular sample in a manner hereinafter described. Solenoid-operated pinch valves 58, 60 are positioned to occlude tubes 28 and 44, respectively, in proximity to the reagent sources 30, 50, respectively. Air pumps 62, 64 are interposed in tubes 66, 68, respectively, which tubes have their outlet ends coupled to tubes 28 and 44, respectively, downstream of the corresponding pinch valves. Compressible tubes 70, 72 have their outlet ends coupled to tubes 28, 44, respectively, downstream of the coupling of tubes 66, 68 to the tubes 28, 44, respectively, and have their inlet ends disposed in sources 74, 76, respectively, of pilot fluids such as water. The aforementioned coupled outlets of tubes 70, 72 are upstream of the pumps 26, 48, respectively. Solenoid operated pinch valves 78, 80 are positioned to occlude tubes 70, 72, respectively.

The pinch valves 58, 60, 78, 80 and the air pumps 62, 64 are controlled by a control device 82 associated with the sampler 10 through a programmer 84. The control device 82 is a code or character recognition device which may be of the optical type such as manufactured by Welch Allyn, Inc. of Skaneateles Falls, N.Y. It may read either the reagent requirements of the samples for the different analyses or the channels or the reagents which are not required for the samples. The code or characters, not shown, associated with each sample may be supplied on label portions 86 of each sample holder which holder may be formed similarly to the sample holders of Engelhardt U.S. Pat. No. 3,781,120. The analysis requirements of a sample are read by the control device 82 prior to one incremental indexing movement of the turntable 12 to the position of the sample holder 18 of FIG. 1. The illustrated position of the sample holder 18 is the sample offtake position. The signal from the control device 82 is directed along lead 88 to the programmer 84. The programmer, on command from the control device 82, energizes the pinch valves 58, 60, 78, 80 along leads 90, 92, 94, 96, respectively, and energizes air pumps 62, 64, along leads 98, 100, respectively.

When constituents of a sample are to be analyzed as described above in both Channel 1 and Channel 12, valves 58 and 60 are open, valves 78 and 80 are closed and air pumps 62 and 64 are deenergized under the influence of control device 82. If the device 82 has transmitted a signal to the programmer 84 to discontinue the supply of reagent to Channel 1 while continuing the supply of reagent to Channel 12 for the sample in the holder 18, the constituent of that sample, glucose, is analyzed as described in Channel 12, while the programmer 84 is operative, in timed or phased relation to entry and mixture of the previous sample with reagent in tube 28, to close valve 58 and open valve 78. This results in discontinuance of the supply of reagent from the source 30 in tube 28 past the valve 58 and the commencement of the flow of the pilot fluid from the source 74 past the valve 78 and along the tube 28 past the junctions of tubes 32 and 24. The pilot fluid is segmented by gas from the tube 32, and this stream, together with the addition thereto of the stream supplied by the tube 24 which comprises the sample from the holder 18, displaces the preceding samples downstream in the tube 28 through the mixing coil 34, the heating bath 36, the flowcell 38 and to waste at the same flow rate. In this manner, such preceding samples are analyzed in Channel 1. From the foregoing, it will be apparent that under the influence of the control device 82, the supply of reagent in Channel 12 from the source 50 for the sample in the holder 18 may be discontinued and the flow of pilot fluid from the source 76 substituted in the tube 44. This may take place concurrently with the conditions described last in Channel 1, or may take place in Channel 1 as the last-mentioned sample is analyzed in the manner previously described, depending on the command of the control device 82.

When the control device 82 commands that the supply of reagent be recommenced in Channel 1, for example, for a sample, the responsive programmer 84 is operative, in timed or phased relation to the entry of that sample into the tube 28 from the tube 24, to once again open valve 58 and close valve 78. This results in recommencing the supply of reagent from the source 30 in the tube 28 past the valve 58 and discontinuance of the flow of the pilot fluid past the valve 78. Substantially concurrently therewith, the air pump 62 is energized momentarily by the programmer to admit to tube 28 through tube 66 a volume of air sufficient to form approximately two or three air segments into the liquid therein upstream of the junction of the pilot fluid tube 70 with the tube 28. Such air segments cleanse the inner wall surface of the tube 28 to effectively reduce contamination of the reagent flowing past the valve 58. From the foregoing, it will be apparent that under the command of the control device 82 with reference to the last-mentioned sample that in Channel 12 the flow of reagent from the source 50, if previously discontinued, is recommended in like manner.

In FIG. 2, there is illustrated a manifold or channel of alternative form which is shown substituted in the liquid sample analyzer of FIG. 1 for Channel 1. As will be apparent hereinafter a channel such as shown in FIG. 2 may be substituted for Channel 12 of FIG. 1. In FIG. 2, compressible pump tubes 102, 104 and 106, corresponding to previously described pump tubes 24, 28 and 32, respectively, with similar functions, extend through continuously operated pump 108 similar to pump 26. The inlet end of tube 102 is coupled to one of the outlets of the T connection of the probe 14. The inlet end of the tube 104 is disposed in a source 110 of a liquid reagent. The tube 104 has interposed therein a mixing coil 112, a heating bath 114 and a flowcell 116 in a manner similar to the tube 28. The elements 112, 114, 116 correspond to the elements 34, 36, 38, respectively, heretofore described. A tube 118 has an inlet end coupled to the outlet of tube 104. Intermediate the ends of the tube 118 there is a rising outlet portion 120 directed to waste at atmospheric pressure. The other end of the tube 118, an outlet end, is coupled to the inlet end of a compressible tube 122 having an outlet end coupled to the tube 104 upstream of the pump 108. A pinch valve 124, similar to the pinch valve 78 previously described, cooperates with the tube 122 and has a lead 126 from the programmer 84 shown in FIG. 1. A pinch valve 128, similar to the pinch valve 58 previously described, cooperates with the tube 104 and has a lead 130 from the programmer 84. An air pump 132, similar to air pump 62, is interposed in tube 134, similar to tube 66, which has an outlet coupled to the tube 104. The air pump 132 is energized through a lead 136 from the programmer 84.

When a sample is to be analyzed in the channel of FIG. 2 and therefore mixed with reagent in such channel under the command of the control device 82 of FIG. 1, pinch valve 124 is closed and pinch valve 128 is opened through the programmer 84 in timed or phased relation so that the last-mentioned sample on entering the tube 104 from the tube 102 is mixed with reagent from the source 110. As the sample stream continues flowing in the tube 104 the last-mentioned sample is analyzed in the flowcell 116 for the particular sample constituent, and the sample stream leaving the tube 104 enters the tube 118 and at the rising discharge portion 120, after backing up at the closed valve 124 in the tube 122, the stream is discharged to waste. This condition continues unless or until under the command of the control device 82 a sample is not to be mixed with the reagent and analyzed for the constituent. When this occurs, the responsive programmer 84 in timed or phased relation to the entry of the last-mentioned sample into the tube 104 from the tube 102 discontinues the supply of reagent from the source 110 for that sample by closing the valve 128 and opening the valve 124. When the valve 124 is opened, the segmented stream flowing in the tube 118 becomes a pilot fluid less the gas volume supplied by tube 106 and a volume of fluid equal to the fluid volume supplied by tube 102 which leaves the stream through the discharge portion 120. The remainder of the stream continuing to flow in tube 118 downstream from the discharge portion 120, which constitutes the pilot fluid, flows into the tube 122 from which it is outletted into the tube 104 for recirculation and flow therealong and segmentation by gas supplied from the tube 106 to provide in part a pilot fluid. The flow from the tube 102, which comprises the last-mentioned sample, is added to the segmented pilot fluid, and the resulting stream displaces the preceding sample-reagent combinations downstream in the tube 104 through the mixing coil 112, the heating bath 114 and the flowcell 116 and from the tube 104 into the tube 118. In this manner, such preceding samples are analyzed in the channel.

When the control device 82 of FIG. 1 commands that the supply of reagent be recommenced in the channel of FIG. 2 for a sample, the responsive programmer 84 is operative, in timed or phased relation to the entry of that sample into the tube 104 from the tube 102, to once again open valve 128 and close valve 124. This results in recommencing the supply of reagent from the source 110 in the tube 104 past the valve 128 and discontinuance of the flow of the pilot fluid past the valve 124. Substantially concurrently therewith, the air pump 132 is energized momentarily by the programmer to admit to the tube 104 through the tube 134 a volume of air sufficient to form approximately two or three air segments in the liquid therein upstream of the junction of the pilot fluid tube 122 with the tube 104. Such air segments cleanse the inner wall surface of the tube 104 and such surfaces of the components 112, 114 and 116 therein to effectively reduce contamination of the reagent flowing past the valve 128. The stream outletted from the tube 104 into the tube 118 is once again discharged to waste through the discharge portion 120 in the manner previously described.

While plural forms of the invention have been illustrated and described, it will be apparent, especially to those versed in the art, that the invention may take other forms and is susceptible of various changes in details without departing from the principles of the invention.

What is claimed is:

1. A liquid sample analyzer, comprising: means for flowing a stream of discrete respective aliquots of successive samples along first and second conduits from a sampler, said first and second conduits each including first means for reacting said aliquots of successive samples with a reagent and second means for viewing the reaction product, means for introducing a different reagent into each of said first and second conduits upstream of said first means thereof to form in each of said conduits a sample-reagent mixture, control means for identifying said successive samples at said sampler, and means responsive to said control means for discontinuing said introduction of said different reagent into either one of said first and second conduits with respect to selected ones of said samples, said control means being operative through said means responsive to said control means to introduce said pilot fluid into one of said first and second conduits while introducing said reagent into the other of said first and second conduits for flow in phased relation displacing said mixture along said first and second means.

2. A liquid sample analyzer, comprising: means for flowing a stream of discrete samples successively along a first conduit from a sampler, said first conduit including first means for reacting said successive samples with a reagent and second means for viewing the reaction product, means for introducing a reagent into said first conduit upstream of said first means thereof to form in said conduit a sample-reagent mixture, control means for identifying said successive samples at said sampler, and means responsive to said control means for discontinuing said introduction of said reagent into said first conduit with respect to selected ones of said samples and for substituting therefor a pilot fluid in phased relation displacing said mixture at the same flow rate along said first conduit, said means for substituting of pilot fluid for said reagent comprising a second conduit having an inlet end communicating with said first conduit down stream from said viewing means thereof for recirculating said sample-reagent mixture through the outlet selectively in connection with said first conduit upstream of said first means thereof.

3. Apparatus as defined in claim 1, wherein: said means for introducing said pilot fluid comprises a third conduit having an inlet communicating with said one of said conduits into which said pilot fluid is introduced, said inlet being downstream from said viewing means, for recirculating said sample-reagent mixture through an outlet selectively in communication with the last-mentioned conduit upstream of said first means thereof.

4. A method of analyzing liquid samples comprising the steps of:
flowing a stream of discrete aliquots of successive samples along respective first and second conduits from a source, each of which conduits includes a portion for reacting the successive samples with reagents and a portion for viewing the reaction product;
introducing a different reagent into said first and second conduits upstream of the reaction portion of each of the said conduits to form a sample-reagent mixture;
identifying the successive samples at the source; and
responsive to such identification discontinuing the introduction of said different reagent into either one of said first and second conduits and substituting therefor a pilot fluid for said reagent in one of said first and second conduits while introducing said reagent into the other of said first and second conduits for flow in phased relation at the same flow rate along the reacting and viewing portions.

5. A method of analyzing liquid samples comprising the steps of:
flowing a stream of discrete samples along a first conduit from a source, the conduit including a portion for reacting the successive samples with a reagent and a portion for viewing the reaction product;
introducing a reagent into said first conduit upstream of the reaction portion of said conduit to form a sample-reagent mixture;
identifying the successive samples at the source;
responsive to such identification discontinuing the introduction of said reagent into said first conduit and substituting therefor in phased relation a pilot fluid displacing the mixture at the same flow rate along the reacting and viewing portions of said first conduit, said pilot fluid introduction including recirculating the sample-reagent mixture passed through said analysis portion as said pilot fluid.

6. A method as defined in claim 4, wherein: said pilot fluid introduction includes recirculating said sample-reagent mixture passed through said viewing portion as a pilot fluid for reintroduction into said first and second conduits upstream of said sample flow thereinto.

* * * * *